(12) United States Patent
Castaldi et al.

(10) Patent No.: US 7,057,068 B2
(45) Date of Patent: Jun. 6, 2006

(54) PROCESS FOR THE PREPARATION OF MODAFINIL

(75) Inventors: Graziano Castaldi, Briona (IT); Vittorio Lucchini, San Donato Milanese (IT); Antonio Tarquini, Tortona (IT)

(73) Assignee: DIPHARMA S.p.A., Mereto Di Tomba (IT)

( * ) Notice: Subject to any disclaimer, the term of this patent is extended or adjusted under 35 U.S.C. 154(b) by 54 days.

(21) Appl. No.: 10/513,881

(22) PCT Filed: Apr. 23, 2003

(86) PCT No.: PCT/EP03/04229

§ 371 (c)(1), (2), (4) Date: Nov. 9, 2004

(87) PCT Pub. No.: WO03/095423

PCT Pub. Date: Nov. 20, 2003

(65) Prior Publication Data

US 2005/0154063 A1    Jul. 14, 2005

(30) Foreign Application Priority Data

May 10, 2002 (IT) .................. MI2002A0991

(51) Int. Cl.
*C07C 233/05* (2006.01)

(52) U.S. Cl. ........................ 564/162; 560/15

(58) Field of Classification Search ........... 564/162; 560/15

See application file for complete search history.

(56) References Cited

U.S. PATENT DOCUMENTS

| 4,062,973 A | 12/1977 | Nickl et al. |
| 4,177,290 A | 12/1979 | Lafon |
| 4,927,855 A * | 5/1990 | Lafon .................. 514/618 |
| 4,964,893 A | 10/1990 | Brannigan et al. |

FOREIGN PATENT DOCUMENTS

| DE | 221 261 | 9/1907 |
| WO | 02/10125 | 2/2002 |

* cited by examiner

*Primary Examiner*—Shailendra Kumar
(74) *Attorney, Agent, or Firm*—Young & Thompson

(57) ABSTRACT

A process for the preparation of 2-[(diphenylmethyl)sulfinyl]acetamide (I) comprising the oxidation of sodium 2-[(diphenylmethyl)sulfenyl]acetate to the corresponding sulfoxide and the derivatization of the latter to amide

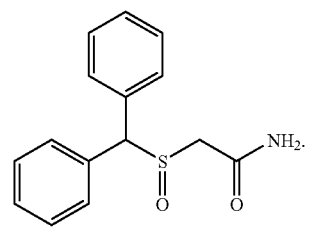

(1)

7 Claims, No Drawings

PROCESS FOR THE PREPARATION OF MODAFINIL

This application is a 371 of PCT/EP03/04229, filed Apr. 23, 2003.

FIELD OF THE INVENTION

The present invention relates psychostimulants, in particular to a novel process for the preparation of 2-[(diphenylmethyl)sulfinyl]acetamide (1), also known as modafinil.

TECHNOLOGICAL BACKGROUND

Modafinil (1) is an $\alpha_1$-adrenergic agonist having psychostimulant activity, used for the treatment of idiopathic narcolepsy.

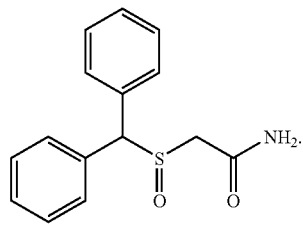

(1)

At present, a number of known synthetic procedures (U.S. Pat. No. 4,177,290, FR 2582038 and EP 0283362) involve as key intermediate 2-[(diphenylmethyl)sulfenyl]acetic acid chloride (2), which is converted to amide (3) by treatment with ammonia and is then oxidized with hydrogen peroxide (scheme 1)

Scheme 1

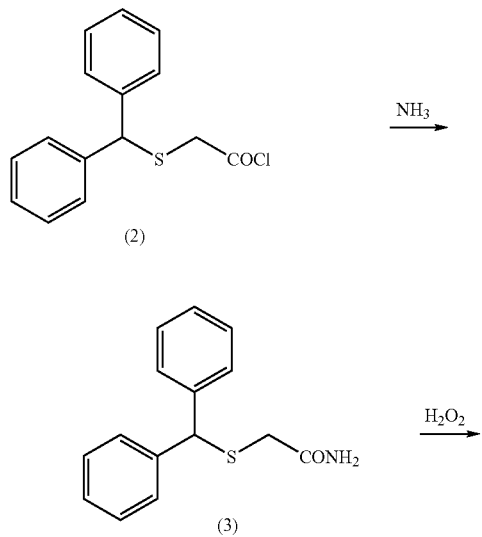

All these methods share the fact that oxidation with hydrogen peroxide is not selective to the sulfoxide, but also affords the sulfone (4):

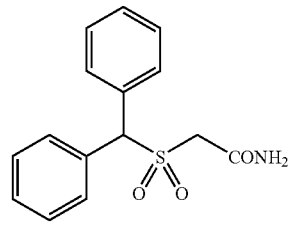

(4)

U.S. Pat. No. 4,177,290 discloses an alternative process for the application on an industrial scale (scheme 2). Benzhydrol (5), thiourea (6) and 2-chloroacetic acid (7) are reacted in the presence of hydrobromic acid to obtain 2-[(diphenylmethyl)sulfenyl]acetic acid (8), which is oxidized with hydrogen peroxide to afford 2-[2-[(diphenylmethyl)sulfinyl]acetic acid (9). This is reacted with $NaHCO_3$ and dimethyl sulfate and the resulting methyl ester (10) is converted to modafinil by treatment with ammonia.

Scheme 2

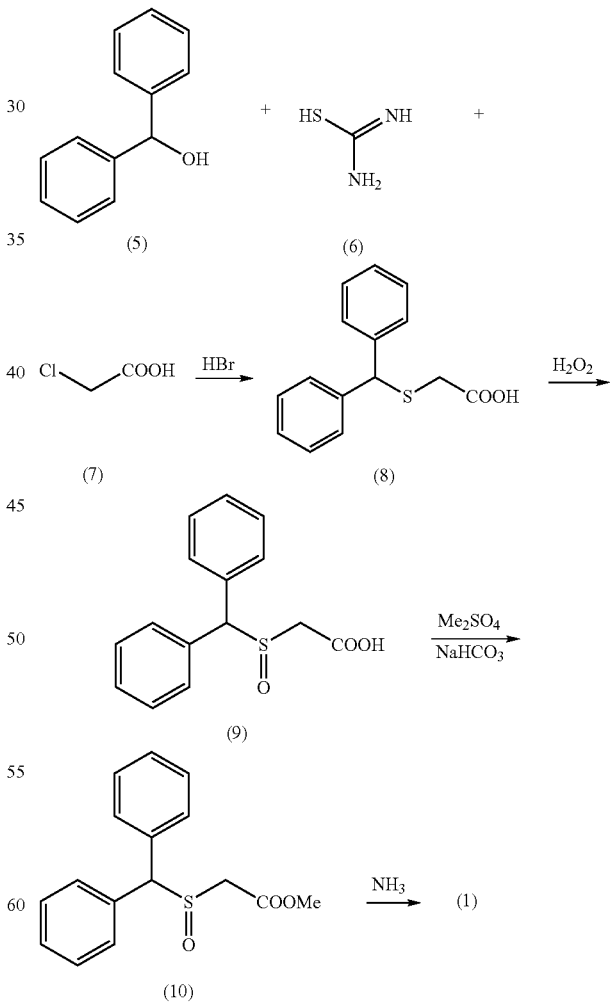

However, the final product is difficult to purify from 2-[2-[(diphenylmethyl)sulfinyl]acetic acid (9) and the methyl ester (10) thereof (two recrystallization steps are necessary) and the overall process yield is 41%. Moreover, the process involves the use of dimethyl sulfate, which is a cancerogenic reagent.

According to EP 0233106 and U.S. Pat. No. 4,927,855, concerning modafinil optically active forms, optically active 2-[2-[(diphenylmethyl)sulfinyl]acetic acid (9) is converted to the methyl ester (10) with NaHCO$_3$ and dimethyl sulfate, then is subjected to a transamidation reaction with ammonia.

WO 02/10125 discloses a method for the preparation of modafinil and its polymorphs by oxidation of 2-[(diphenylmethyl)sulfenyl]acetamide (3) with hydrogen peroxide in the presence of a mineral acid and of an alcohol or a phase transfer catalyst; this overcomes the problem of overoxidation. However, a recrystallization step is necessary to obtain the final product with pharmaceutically acceptable purity. It would therefore be advantageous to provide a method which not only prevents the sulfone formation, but also directly affords modafinil with a pharmaceutically acceptable purity.

DETAILED DISCLOSURE OF THE INVENTION

The present invention relates to a process for the preparation of 2-[(diphenylmethyl)sulfinyl]acetamide (1)

(1)

comprising the following steps:
a) oxidation of sodium 2-[(diphenylmethyl)sulfenyl]acetate (11)

(11)

with sodium hypochlorite to give sodium 2-[(diphenylmethyl)sulfinyl]acetate (12);

(12)

b) hydrolysis of sodium 2-[(diphenylmethyl)sulfinyl]acetate (12) to give 2-[(diphenylmethyl)sulfinyl]acetic acid (9);

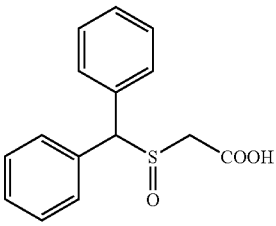

(9)

c) conversion of 2-[(diphenylmethyl)sulfinyl]acetic acid to 2-[(diphenylmethyl)sulfinyl]acetamide by treatment with a condensing agent and ammonia.

Sodium 2-[(diphenylmethyl)sulfenyl]acetate (11) is a known compound, in particular compound (15) is obtained as described in Zhongguo Yaowu Huaxue Zazhi, 9(2), 132–134 (1999) (scheme 3).

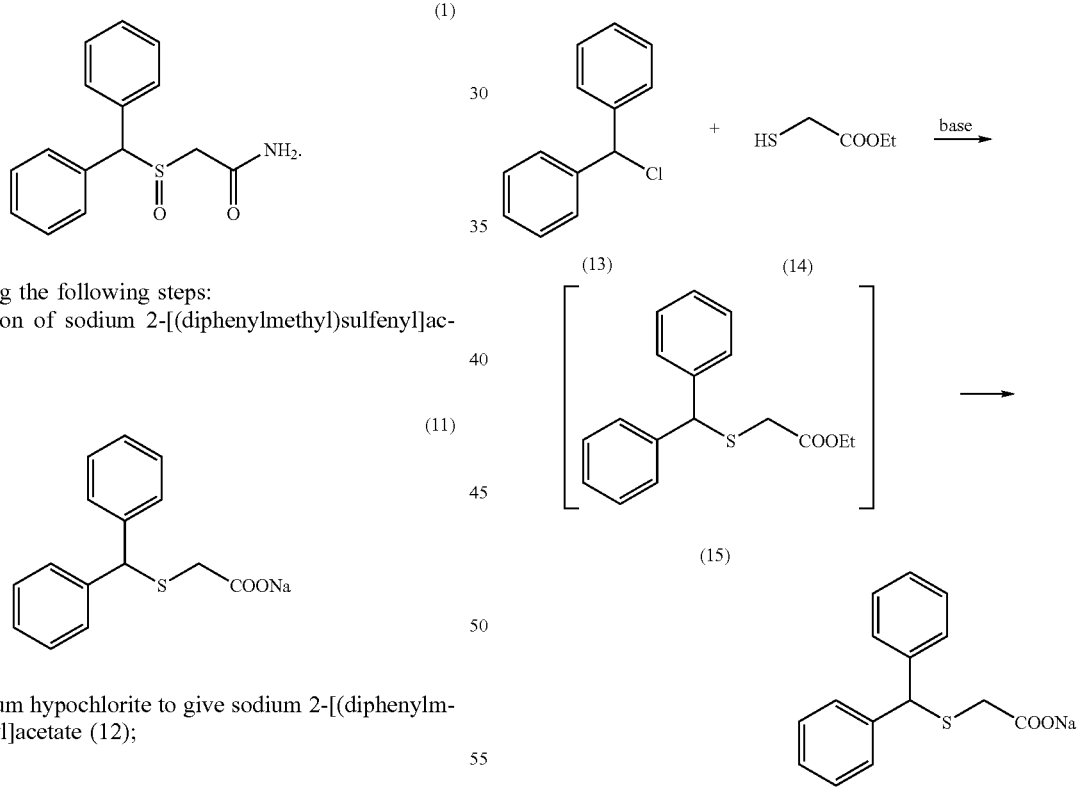

Scheme 3

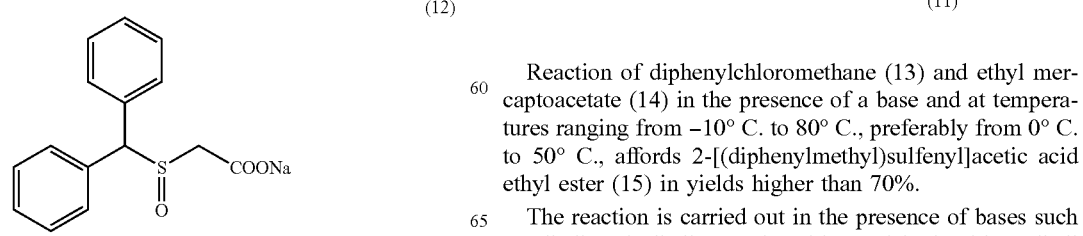

(11)

Reaction of diphenylchloromethane (13) and ethyl mercaptoacetate (14) in the presence of a base and at temperatures ranging from −10° C. to 80° C., preferably from 0° C. to 50° C., affords 2-[(diphenylmethyl)sulfenyl]acetic acid ethyl ester (15) in yields higher than 70%.

The reaction is carried out in the presence of bases such as alkali and alkaline-earth oxides and hydroxides, alkali and alkaline-earth carbonates and bicarbonates, alkoxides and alkoxides in alcoholic solution, in amounts ranging from 1 to 5 equivalents, preferably from 1.1 to 2 equivalents.

The solvent can be selected from toluene, chlorinated solvents, preferably dichloromethane, esters, preferably ethyl acetate, ethers, preferably diethyl ether, tetrahydrofuran, dipolar aprotic solvents, preferably dimethylformamide, cyclohexane, alcohols, preferably methanol, ethanol and isopropanol, ketones, preferably acetone, or a mixture thereof, in amounts ranging from 1 to 10 volumes, preferably from 3 to 6 volumes.

In the process of the present invention the ester of formula (15) is not isolated, but is directly hydrolysed to give the sodium salt (11) in the presence of aqueous solutions of oxides, hydroxides, alkali and alkaline-earth carbonates and bicarbonates in amounts ranging from 1 to 5 equivalents, preferably from 1.1 to 2 equivalents.

According to the invention, oxidation of salt (11) is performed distilling off the water-solvent mixture, taking up the residue with water and treating with a sodium hypochlorite aqueous solution at concentrations ranging from 2 to 30%, preferably from 5 to 15%, in amounts ranging from 1 to 5 equivalents, preferably from 1.1 to 2 equivalents. The reaction is carried out at temperatures ranging from −10 to 80° C., preferably from 10 to 60° C.

After completion of the reaction, the mixture is extracted with an organic solvent, preferably toluene, and the aqueous phase is acidified with mineral acids such as hydrochloric, sulfuric, phosphoric acids, preferably sulfuric acid, to give the corresponding 2-[(diphenylmethyl)sulfinyl]acetic acid (9), in yields of 75÷80% on the isolated product, in substantially pure form and free from the corresponding sulfone. Intermediate compound sodium 2-[(diphenylmethyl) sulfinyl]acetate (12), which can optionally be isolated, is novel and is a further object of the invention.

Transformation of acid (9) into modafinil is carried out by treatment with condensing agents and ammonia. The conventional method of chemical activation of the carboxylic group, i.e. the transformation of the acid into the corresponding chloride, is not compatible with the sulfoxide group (see Oae "Organic Chemistry of Sulfur" Plenum Press N.Y. 1977 page 406), which would be reduced to sulfide under these conditions.

The condensing agent is preferably selected from N,N'-carbonyldiimidazole, N,N'-carbonylditriazole, dicyclohexylcarbodiimide, preferably N,N'-carbonyldiimidazole, in amounts ranging from 1 to 5 equivalents, preferably from 1.1 to 2.0 equivalents. The reaction solvent is selected from toluene, chlorinated solvents, preferably dichloromethane, esters, preferably ethyl acetate, ethers, preferably diethyl ether, tetrahydrofuran, dipolar aprotic solvents, preferably dimethylformamide, cyclohexane, ketones, preferably acetone, in amounts ranging from 1 to 10 volumes, preferably from 3 to 6 volumes. According to a preferred embodiment of the invention the solvent is dichloromethane. The reaction is carried out at a temperature ranging from −10 to 50° C., preferably from 0 to 20° C.

The reaction proceeds through a reactive intermediate which is not isolated and which is reacted with gas ammonia at a temperature ranging from −10 to 30° C., preferably from 0 to 10° C., to yield modafinil. Ammonia can be used either in gaseous phase or in aqueous solution, at concentrations ranging from 5 to 30% and in amounts ranging from 1 to 5 equivalents, preferably from 1.2 to 2 equivalents.

The product is obtained in yields of 70÷75% with respect to [(diphenylmethyl)sulfinyl]acetic acid and with % HPLC purity>99.5%.

The invention is illustrated in greater detail by the following examples.

EXAMPLES

Example 1

Preparation of 2-[(diphenylmethyl)sulfinyl]acetic Acid (9)

81.5 g of a 21% sodium ethoxide solution in ethanol (0.237 mols of sodium ethoxide), kept under inert atmosphere, is added with 28.6 g (0.237 mols) of ethyl mercaptoacetate (14). The stirred mixture is heated to 30÷35° C. inner temperature and 45 g (0.22 mols) of diphenylchloromethane (13) are added thereto in 15'. After completion of the addition, the mass is kept under stirring at 30÷35° C. for 4 h. After completion of the reaction, 24 ml of a 30% sodium hydroxide solution (0.239 mols) are added in 15÷20', keeping the inner temperature at 30÷35° C. After completion of the addition, the mixture is kept under stirring for about 30', then solvents are distilled off until reaching inner temperature of 100° C., gradually adding an equal volume of water to the distillate during the operation.

The mass is cooled to 40÷45° C. inner temperature and 360 ml of a 5% sodium hypochlorite aqueous solution (0.24 mols) are added, in about 2 hours.

15' After the end of the addition, the mass is cooled to 20÷25° C. inner temperature, added with 180 ml of toluene and acidified with 88 ml of 50% sulfuric acid, keeping pH at 2; the precipitated product is filtered, washed with water to neutrality, then squeezed and dried in oven under vacuum at a temperature of 55÷60° C., thereby obtaining 44 g (0.16 mols) of 2-[(diphenylmethyl)sulfinyl]acetic acid (9) (yield: 73%).

$^1$H-NMR (CDCl$_3$, δ ppm): 3.20÷3.25 (d, 1H); 3.63÷3.68 (d, 1H) (J=12 Hz); 5.29 (s, 1H); 7.38÷7.49 (m, 10H)

Example 2

Preparation of 2-[(diphenylmethyl)sulfinyl]acetamide (Modafinil)

Method 1

A solution of 10 g (0.036 mols) of 2-[(diphenylmethyl) sulfinyl]acetic acid (9) in 66 g of dichloromethane cooled at 15° C. is added with 6.8 g (0.042 mols) of N,N'-carbonyldiimidazole in 5 portions of 1.3 g each. After completion of the addition, the mass is cooled to 0÷5° C. and gas ammonia is bubbled therein. After that, the inner temperature is brought to 20÷25° C. keeping these conditions for about 30', then the mixture is diluted with 50 ml of water. The phases are separated, the organic phase is added with 40 ml of water and dichloromethane is distilled off at atmospheric pressure.

The mass is cooled to 20÷25° C. and added with 20 ml of ethyl acetate, keeping stirring for about 1 hour; the precipitate is filtered, washed with water to obtain 6.9 g (0.025 mols) of 2-[(diphenylmethyl)sulfinyl]acetamide (modafinil) (yield: 70%, HPLC purity>99.5%).

$^1$H-NMR (CDCl$_3$, δ ppm): 3.22÷3.27 (d, 1H); 3.63÷3.68 (d, 1H) (J=12 Hz); 5.32 (s, 1H); 7.38÷7.49 (m, 10H).

Example 3

Preparation of 2-[(diphenylmethyl)sulfinyl]acetamide (Modafinil)

Method 2

A solution of 20 g (0.073 mols) of 2-[(diphenylmethyl)sulfinyl]acetic acid (9) in 132 g of dichloromethane cooled at 15° C. is added with 13.6 g (0.084 mols) of N,N'-carbonyldiimidazole in 5 portions of 2.7 g each. After completion of the addition, the mass is cooled to 0÷5° C. and added with 120 ml (1.06 mols) of a 15% aqueous ammonia solution. After that, the inner temperature is brought to 20÷25° C. keeping these conditions for about 30', then the mixture is diluted with 100 ml of water. The phases are separated, the lower organic phase is added with 80 ml of water and dichloromethane is distilled off at atmospheric pressure.

The mass is cooled to 20÷25° C. and added with 40 ml of ethyl acetate, keeping stirring for about 1 hour; the precipitate is filtered and washed with water to obtain 14.4 g of 2-[(diphenylmethyl)sulfinyl]acetamide (modafinil) (yield: 72.2%, HPLC purity>99.5%).

$^1$H-NMR (CDCl$_3$, δ ppm): 3.22-3.27 (d, 1H); 3.63÷3.68 (d, 1H) (J=12 Hz); 5.32 (s, 1H); 7.38÷7.49 (m, 10H).

The invention claimed is:

1. A process for preparation of 2-[(diphenylmethyl)sulfinyl]acetamide (1)

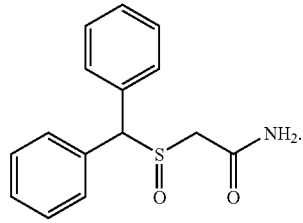

(1)

comprising the following steps:

a) oxidation of sodium 2-[(diphenylmethyl)sulfenyl]acetate (11)

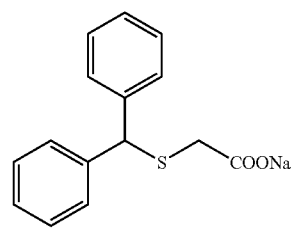

(11)

with sodium hypochlorite to give sodium 2-[(diphenylmethyl)sulfinyl]acetate (12)

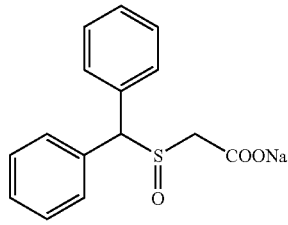

(12)

b) hydrolysis of sodium 2-[(diphenylmethyl)sulfinyl]acetate to give 2-[(diphenylmethyl)sulfinyl]acetic acid (9)

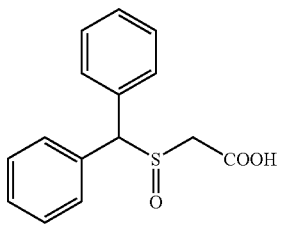

(9)

c) conversion of 2-[(diphenylmethyl)sulfinyl]acetic acid (9) to 2-[(diphenylmethyl)sulfinyl]acetamide (1) by treatment with a condensing agent and ammonia.

2. A process as claimed in claim 1, wherein the condensing agent is selected from N,N'-carbonyldiimidazole, N'N'-carbonylditriazole and dicyclohexylcarbodiimide.

3. A process as claimed in claim 2, wherein the condensing agent is N,N'-carbonyldiimidazole.

4. A process as claimed in claim 1, wherein the amount of sodium hypochlorite ranges from 1 to 5 equivalents.

5. A process as claimed in claim 4, wherein the amount of sodium hypochlorite ranges from 1.1 to 2 equivalents.

6. A process as claimed in claim 1, wherein sodium hypochlorite is used in aqueous solution at concentrations ranging from 2 to 30%.

7. A process as claimed in claim 6, wherein sodium hypochlorite is used in aqueous solution at concentrations ranging from 5 to 15% sodium.

* * * * *